United States Patent [19]

Matishev

[11] 4,070,410

[45] Jan. 24, 1978

[54] METHOD OF ISOLATING INDIVIDUAL NORMAL ALKANES FROM PETROLEUM STOCK

[76] Inventor: Vladimir Alexandrovich Matishev, Novocheremushkinskaya ulitsa, 64, korpus 3, kv. 19, Moscow, U.S.S.R.

[21] Appl. No.: 714,752

[22] Filed: Aug. 16, 1976

[51] Int. Cl.$^2$ .............................................. C07B 21/00
[52] U.S. Cl. ............................... 260/676 R; 208/308; 260/96.5 C
[58] Field of Search .................. 208/308; 260/96.5 C, 260/676 R

[56] References Cited

U.S. PATENT DOCUMENTS

| | | | |
|---|---|---|---|
| 2,588,602 | 3/1952 | Adams et al. | 260/676 R |
| 2,672,457 | 3/1954 | Weedman | 260/676 R |
| 3,506,569 | 4/1970 | Yata et al. | 260/676 R |

*Primary Examiner*—Herbert Levine
*Attorney, Agent, or Firm*—Haseltine, Lake & Waters

[57] ABSTRACT

A method of isolating individual normal alkanes from petroleum stock, wherein the petroleum stock is contacted with crystalline carbamide in the presence of an activator at a temperature which is the upper limit for a given individual normal alkane to be isolated, having maximum molecular weight for the given stock, to complex with crystalline carbamide, the result being a complex of said alkane with the carbamide. The residual stock is taken off from the complex formed. The complex is washed with an individual normal alkane similar to the isolated one, heated up to the temperature 2°–5° C higher than its decomposition point and the individual normal alkane, having maximum molecular weight for the given stock, is isolated. Individual normal alkanes are isolated in succession in order of decreasing molecular weights from the stock taken off from the formed complex of the normal alkane, following the technology described above.

The proposed method provides individual normal alkanes up to 99.99 mass.% pure and is simple in technology.

1 Claim, No Drawings

METHOD OF ISOLATING INDIVIDUAL NORMAL ALKANES FROM PETROLEUM STOCK

The present invention relates to isolating individual normal alkanes from petroleum stock.

Said normal alkanes (paraffins) find wide application in different fields of petrochemistry. They are employed in production of synthetic fatty acids, higher fatty alcohols, alpha-olefins, biodegradable surfactants (including soft detergents), chlorinated paraffins used for manufacturing additives to lubricants, fire-resistant tissues and paper. Microbiological synthesis is one of the most important fields of application of normal alkanes, namley, the production of artificial protein for fattening cattle and poultry.

More and more rigid requirements are imposed on normal alkanes which is a raw material for all the above-cited productions with respect to the content of the main substance, namely, n-alkanes and impurities, especially aromatic hydrocarbons. The most rigid requirements are imposed on a raw material for producing higher fatty alcohols, artificial protein, and biodegradable sulphonates obtained by sulphoxidation. This raw material must contain no more than 0.01% of aromatics, no less than 99.0% of the main substance, and when employed in the production of protein, no 3,4-benzopyrene at all which is a carcinogenic compound.

n-Paraffins used in the above-cited productions most often are of $C_{10}$-$C_{24}$ composition.

Highly pure individual n-paraffins are the most promising raw material for detergents, emulsifiers, and additives.

Known in the art are methods of isolating a mixture of normal alkanes for industrial purposes.

One of the known methods resides in that a mixture of hydrogen and carbon oxide is passed over an iron-containing catalyst at 160–420° C or over cobalt and magnesium-containing catalyst at 160–200° and under a pressure of 8–10 atg. A mixture of normal paraffin hydrocarbons known as Fischer-Tropsch wax is formed boiling out within a temperature range depending on experimental conditions. Said Fischer-Tropsch wax is fractionated with the help of usual atmospheric-vacuum distillation into gasoline, kerosene, and gas oil fractions, vacuum distillates, and distillation residue. For isolating individual n-alkanes, each of the fractions obtained is subjected to precise rectification, the result being narrow fractions, or concentrates, containing 70–90 wt % of individual n-alkanes.

Each of said concentrates is subjected to repeated precise rectification, the result being n-alkanes, containing 94–97 wt % of the main substance.

In order to obtain n-alkanes of the required degree of purity, an additional purification of said n-alkanes with sulphuric acid is needed with subsequent neutralization by an aqueous alkaline solution, washing off the alkali with water, drying, and recrystallization under isothermal conditions.

Another method of isolating normal alkanes resides in isolating a mixture of n-alkanes from petroleum distillates using molecular sieves. The method requires fractionation and purification of the products obtained.

Methods based on application of carbamide are the most promising for isolating n-alkanes from petroleum stock. In some of these methods carbamide is used in a crystalline state, while in others in the form of solutions, for example, aqueous. The methods are performed by different technologies using reactors either with stirring the reaction mass or with pumping the initial petroleum stock through a stationary bed of the crystalline carbamide on the support.

Said methods provide isolation of only a mixture of n-paraffins from a stock without their separation at this stage into individual components. Purity of such total paraffins without additional purification is 97–99%. To obtain individual n-paraffins 99.0–99.5 wt % pure with respect to the main component, in addition to the stage of isolating a mixture of n-paraffins from hydrocarbon stock the following stages of additional purification are needed:

a. rectification with a number of columns equal to that of the individual hydrocarbons to be isolated;

b. sulfuric acid, and/or adsorptive, and/or hydropurification of each individual n-paraffin;

if sulfuric acid additional purification is used, washing of every individual n-paraffin with an aqueous solution of alkali up to a neutral reaction is required;

c. isothermal recrystallization of each individual n-paraffin.

Thus, in order to obtain one individual n-alkane which is 99.0–99.5% pure, all the best known methods involve no less than 4–5 stages.

It is an object of the invention to provide a method of isolating individual normal alkanes from petroleum stock.

According to the invention, the method resides in that petroleum stock is contacted with crystalline carbamide in the presence of an activator at a temperature which is the upper limit for a given individual normal alkane to be isolated, having maximum molecular weight for the given stock, to complex with the crystalline carbamide, the result being a complex of said alkane with the carbamide, with subsequent taking off of the residual stock from said complex, washing the complex with an individual normal alkane similar to the isolated one, and heating said complex up to the temperature 2°–5° higher than its decomposition point with isolating the individual normal alkane, having maximum molecular weight for the given stock; individual normal alkanes are isolated in succession in order of decreasing molecular weights from the stock taken off from said complex following the above-cited technology.

It is known that any n-alkane complexes with carbamide in a wide temperature range, being not restricted to the lower temperature limit.

The upper limit of complexation is the maximum temperature at which the complexing of an individual n-alkane with crystalline carbamide begins and quantitatively completes.

If n-alkane and carbamide are not pure enough, the complexation is performed in the presence of an activator.

Acetone, methylethylketone, lower alcohols, and other known activators can be used as an activator.

The amount of the activator depends on chemical composition of the stock and is proportional to the content of the compounds inhibiting complexation (resinous substances, active sulfide compounds, and the like).

In order to isolate the given n-alkane at a temperature of the upper limit of complexation with crystalline carbamide from the multicomponent mixture with other hydrocarbons, it is essential that said n-alkane have maximum molecular weight in this mixture (with maximum $n$). Thus, if all n-alkanes with $n = 10$–24 are present in the mixture, only n-alkane with $n=24$ must be isolated at first.

Normal alkanes with a number of carbon atoms in the molecule $n<24$ cannot complex with carbamide at a temperature of the upper limit of complexation of normal alkane with $n=24$, since the temperature of the upper limit of their complexation with carbamide is lower than that of n-alkane with $n=24$.

After complete binding of n-alkane with $n=24$ to the complex it is possible to isolate n-alkane with $n=23$, and so on, in order of decreasing molecular weights, until all individual normal alkanes containing in the stock are totally isolated.

The temperature of the upper limit of the complexing of individual n-alkane with carbamide in a multicomponent mixture can be calculated by the equation:

$$\theta_{mix} = \theta - C^{0.609} \sum_{i=3}^{\infty} C_i a_i$$

where
- $\theta$ is the temperature of the upper limit of complexation of the given individual n-alkane with carbamide, ° C;
- $\theta_{mix}$ is the temperature of the upper limit of complexation of the same n-alkane in the multicomponent mixture, ° C;
- $a_i$ is the gradient of a decrease in the temperature of the upper limit of complexation per unit of an increase in mass concentration of the $i$-th component in the multicomponent mixture, ° C/mass % C is the total mass concentration of all $i$ components except the isolated one, mass. %;
- $C_i$ is the mass concentration of the $i$-th component of the multicomponent mixture, mass.%.

By $i$-th component is implied any component of the mixture except the one being isolated.

The second condition necessary for isolating the given individual n-alkane from the multicomponent mixture is the washing of the complex of said n-alkane with crystalline carbamide by the n-alkane similar to that entering into the complex. Such washing removes all other components of the multicomponent mixture from the intercrystalline space of the complex. Said space will be filled with an individual n-alkane identical to that entering into the complex. The amount of the washing agent grows proportionally to the mass of the crystalline carbamide taken for isolating the given n-alkane. After decomposing such a complex, the system contains only the crystalline carbamide and the individual n-alkane which is taken out from the system as commercial end product.

The temperature interval of decomposition of the complex of the given n-alkane with carbamide is limited by the temperature of the upper complexation limit and the decomposition temperature of the carbamide itself.

As a result of isolating n-alkanes from multicomponent systems at temperatures of their upper complexation limits with carbamide, followed by washing of complexes with n-alkanes identical to those entering into said complexes, and decomposing the complexes, individual alkanes are obtained not less than 99.99 mass.% pure which do not contain aromatic impurities. The technology is much simpler than that of known methods since n-alkanes obtained by the proposed method do not require additional purification.

The method is simple in technology and accomplished as follows.

The method can be realized under the conditions of mechanical stirring, fluidization, and in a stationary bed of crystalline carbamide.

It is preferable to isolate n-alkanes from petroleum stock in a stationary bed of crystalline carbamide, which requires a separate reactor block for each individual n-alkane. A reactor block consists of three reactors, identical in design, operating in an alternating cyclic mode and united in an apparatus of the column type.

Three stages of the same cycle take place in each reactor in succession:

(a) complexation, (b) washing of the complex, (c) decomposition of the complex.

COMPLEXATION

Petroleum stock and ethyl alcohol (activator) are mixed in a T-connection. The obtained mixture is heated in a heat-exchanger up to the temperature of the upper limit of complexation of n-alkane with $n$ carbon atoms in the molecule ($\theta_{mix}$) and fed into the bottom part of one of the three reactors loaded with crystalline carbamide. A bed of crystalline carbamide in this reactor is pre-heated up to the same temperature.

As the raw mixture passes through the bed of crystalline carbamide, it enters into the reaction of complexing with the n-alkane having $n$ carbon atoms in the molecule.

The complexation stage is considered to be completed when the calculated amount of raw material passes upwards through the reactor.

A "jump-through" of the isolated alkane is impermissible, since the traces of n-alkanes with $n$ carbon atoms in the molecule contaminate n-alkane with $n$-1 carbon atoms being isolated in the next block. The product leaving the top of the first reactor of the first block and not containing the traces of n-alkane with $n$ carbon atoms in the molecule is delivered to the first reactor of the second identical block for isolating n-alkane with $n$-1 carbon atoms.

Upon completion of the complexation in the first reactor of the first block the flow of the initial petroleum crude is delivered to the second reactor of the first block where the stage of isolating n-alkane with $n$ carbon atoms in the molecule begins, while the stage of washing the complex begins in the first reactor of the first block.

WASHING OF THE COMPLEX n-Alkane with $n$ carbon atoms in the molecule is put into the bottom part of the first reactor of the first block through a steam preheater. Said n-alkane washes off the hydrocarbons of the stock have not reacted with carbamide, from the surface of the complex crystals.

The washing agent (n-alkane with n-carbon atoms in the molecule) contaminated with the washed components of the stock leaves the top part of the first reactor of the first block. The first 10–12 mass.% of said agent are the most contaminated. They are mixed with the initial petroleum stock as a recycle. The rest 88–90 mass.% of the washing agent are used in the same reactor as a washing agent in the following cycle of isolating n-alkane with $n$ carbon atoms in the molecule.

Washing is accomplished at a temperature above that which is the upper limit for n-alkane with $n$ carbon atoms in the molecule to complexate with carbamide and below the decomposition temperature of the complex formed.

The washing stage is considered to be completed when the washing agent at the output of the reactor is identical in its quality to that at the input of said reactor.

From this time on, the complexation stage starts in the third reactor of the first block, the washing stage in the second, and the decomposition stage in the first reactor.

DECOMPOSITION OF THE COMPLEX

Decomposition of the complex is performed by heating up to the temperature 2°-5° C above the complex decomposition point. This results in isolating individual n-alkane which is taken off from the first block as a highly pure end product.

Thus, the first block consisting of three reactors operates, as a whole, continuously, although each of the reactors works within an alternating cyclic regime.

In a similar way, n-alkane with $n-1$ carbon atoms in the molecule is isolated in the second block; n-alkane with $n-2$ carbon atoms is isolated in the third block and so on, until all the n-alkanes are isolated from the initial petroleum stock.

For a better understanding of the present invention specific examples of its realizing are given hereinbelow by way of illustration.

EXAMPLE 1

Petroleum stock which is a straight run petroleum fraction boiling out at 150°-240° C and taken out from an industrial rectifying column with 10 plates at a mass spraying ratio 1.5:1 has the following composition (in mass.%) determined chromatographically:

| | |
|---|---|
| n-tetradecane | 6.24 |
| n-tridecane | 9.72 |
| n-dodecane | 24.84 |
| n-undecane | 20.14 |
| n-decane | 5.74 |
| n-nonane | 1.32 |
| components not forming complexes with carbamide | 32.00 |
| Total | 100.00 |

ISOLATION OF N-TETRADECANE

According to the equation $$\theta_{mix} = \theta - C^{0.609} \Sigma\, C_i a_i$$

the process of isolating n-tetradecane from said petroleum stock is performed at a temperature:

$$\theta_{mix} = 86.0 - 93.76^{0.609} \cdot (9.72 \cdot 0.0037 + 24.84 \cdot 0.0076 + 20.14 \cdot 0.01 + 5.74 \cdot 0.0156 + 1.32 \cdot 0.0196 + 32.0 \cdot 0.0360) = 58.6° C$$

in a stationary bed of crystalline carbamide at a total load 10 kg. The process is run at a mass ratio of carbamide: tetradecane equal to 3.5:1. 10/3.5=2.857 kg of n-tetradecane can be isolated from the given stock with the above-cited load 2.857·100/6.24=45.8 kg of the initial stock is pumped upwards through the carbamide stationary bed. The process is performed in the presence of an activator, namely, ethyl alcohol, in the amounts of 3 mass % per carbamide load. The activator can be introduced into the stock either at once, or portion-wise during the whole process with the help of a metering pump; it can also be introduced continuously. Upon completion of the complexation, the product, leaving the reactor with a stationary bed of crystalline carbamide and not containing n-tetradecane, is fed into the identical reactor of the second block for isolating n-tridecane; the complex formed is washed with n-tetradecane in amounts 3:1 in mass per carbamide for removing unreacted components from the intercrystalline space of the complex. The complex is washed at 58.6° −86.0°. The first 10–12 mass.% of the most contaminated washing agent (n-tetradecane) leaving the reactor are used as a recycle in the following cycle of n-tetradecane isolation; the rest 88–90 mass.% are used as a washing agent in the following cycle. The washed complex is decomposed at 120° C and isolated liquid n-tetradecane is taken off from the reactor. n-Tetradecane isolated in the first cycle is 99.8–99.9 mass % pure; beginning with the second or at most, the third cycle the purity is not less than 99.99 mass %, aromatic hydrocarbons being completely absent.

The process can also be accomplished under the conditions of mechanical stirring or fluidization within the given temperature range and stock to reagents ratio.

ISOLATION OF N-TRIDECANE

The raw material is the product from the first reactor of the first block not containing n-tetradecane and having the following composition (in mass.%):

| | |
|---|---|
| n-tridecane | 10.37 |
| n-dodecane | 26.49 |
| n-undecane | 21.48 |
| n-decane | 6.12 |
| n-nonane | 1.41 |
| components do not forming complex with carbamide | 34.13 |
| Total | 100.00 |

The process of isolating n-tridecane is conducted at a temperature:

$$\theta_{mix} = 82.6 - 89.63^{0.609} \cdot (26.49 \cdot 0.004 + 21.48 \cdot 0.0083 + 6.12 \cdot 0.0127 + 1.41 \cdot 0.017 + 34.13 \cdot 0.035) = 57.9° C.$$

The amount of n-tridecane in said raw material is (45.800−2.857)·0.1037=4.453 kg.

15.6 kg of crystalline carbamide are loaded into the reactor. 15.6·0.03=0.468 g of ethanol must be fed into the reaction zone for activation of the complexation process. However, about ⅓ of the alcohol expended in activation of isolating n-tetradecane, i.e. 10·0.03/3 =0.1 kg, which leaves the reactor for isolating n-tridecane together with the product which is a raw material for isolating n-tridecane, enters the reactor. Therefore, about 0.37 kg of ethanol must be fed into the reactor for isolating n-tridecane. Upon completion of the complexation process, the product leaving the reactor and not containing n-tridecane, is delivered to the following identical reactor of the following block for isolating n-dodecane. The complex formed is washed with n-tridecane in the amounts of 3:1 in mass per carbamide. The washing is performed at a temperature range over 57.9°–82.6° C; then the complex is decomposed at 115°–120° C and the isolated end product is taken off from the reactor. The first 10–12 mass.% of the most contaminated washing agent (n-tridecane) leaving the reactor are used as recycle in the following cycle of isolating n-tridecane, whereas the rest 88–90 mass.% as a washing agent in the following cycle.

Beginning with the second or third cycle, n-tridecane is obtained not less than 99.99 mass.% pure, aromatic hydrocarbons being completely absent.

ISOLATION OF N-DODECANE n-Dodecane is isolated by following the procedure described above, the temperature of complexation being $\theta_{mix}=55.2°$ C. Then the complex of n-dodecane with carbamide is washed at 55.2°–78.5° C, decomposed at 115°–120° C, and the end product not less than 99.99 mass.% pure (after the second or third cycle) and not containing aromatic hydrocarbons at all is taken off from the reactor.

ISOLATION OF N-UNDECANE n-Undecane is isolated by following the procedure described above, the temperature of complexation being $\theta_{mix}=52.5°$ C. Then the complex of n-undecane with carbamide is washed at 52.5°–73.9° C, decomposed at 110°–115°, and the end product not less than 99.99 mass % pure (after second or third cycle) and not containing aromatic hydrocarbons at all is taken off from the reactor.

ISOLATION OF N-DECANE n-Decane is isolated by following the procedure described above, the temperature of complexation being $\theta_{mix} = 44.7°$ C. Then the complex of n-decane with carbamide is washed at 44.7°–68.0° C, decomposed at 110° C, and the isolated end product not less than 99.99 mass.% pure (after the second or the third cycle) and not containing aromatic hydrocarbons is taken off from the reactor.

After isolating n-alkanes, namely from n-tetradecane to n-decane inclusive, 15.2 kg of a hydrocarbon mixture is left in the residue which has a temperature of the onset of crystallization −62.8° C and contains 3.9 mass % of n-nonane and 6.3 mass % of aromatic hydrocarbons. Said residue can be used as a component of propellant for civil aviation.

EXAMPLE 2

By analogy with Example 1, from the petroleum fraction boiling out over the temperature range 60°–180° C and having an octane number 42.6 by the motor method which was obtained on an industrial atmospheric plant, n-undecane, n-decane, n-nonane, n-octane, n-heptane, and n-hexane are isolated in succession with a 100% take off in terms of the potential yield for each component and with a purity not less than 99.99 mass,% (after the third cycle), aromatic hydrocarbons being completely absent. The process parameters are given in Table 1. The mass ratio between crystalline carbamide, petroleum stock and activator is 3.5:1:0.105, respectively.

Table 1

| Isolated Component | Concentration in petroleum stock, mass % | Temperature, ° C | | | Mass ratio washing agent: carbamide |
|---|---|---|---|---|---|
| | | complexation | washing of the complex | decomposition of the complex | |
| n-Undecane | 1.22 | 29.4 | 29.4–73.9 | 105–110 | 3.0:1 |
| n-Decane | 3.46 | 17.1 | 17.1–68.0 | 100–105 | 3.0:1 |
| n-Nonane | 7.64 | 15.9 | 15.9–58.0 | 95–100 | 2.8:1 |
| n-Octane | 8.18 | 12.1 | 12.1–48.0 | 90–95 | 2.5:1 |

Table 1-continued

| 1 | 2 | 3 | 4 | 5 | 6 |
|---|---|---|---|---|---|
| n-Heptane | 4.71 | 3.7 | 3.7–38.0 | 85–90 | 2.3:1 |
| n-Hexane | 1.09 | −11.4 | −11.4–+28.0 | 80–85 | 2.0:1 |
| Components not forming complex with carbamide | 73.70 | — | — | — | — |
| Total | 100.0 | — | — | — | — |

After isolating all the above-cited n-alkanes the octane number of the residue of the petroleum fraction 60°–180° C increased by 31 points and became equal to 73.6 according to motor method.

EXAMPLE 3

By analogy with Examples 1 and 2, from the oil fraction boiling within the temperature range 350°–395° and having the solidification temperature 32.4° C, n-tetracosane, n-tricosane, n-docosane, n-heneicosane, and n-eicosane are isolated with a 100% take off in terms of the potential yield for each component with the purity not less than 99.99 mass.% (after the third cycle), aromatic hydrocarbons being completely absent. The process parameters are given in Table 2. The ratio between crystalline carbamide, petroleum stock, and activator is 3.5:1.0:0.105 in mass, respectively.

Table 2

| Isolated Component | Concentration in petroleum stock, mass % | Temperature, ° C | | | Mass ratio washing agent: carbamide |
|---|---|---|---|---|---|
| | | complexation | washing of the complex | decomposition of the complex | |
| n-Tetracosane | 2.56 | 93.9 | 93.9–99.7 | 128–130 | 3:1 |
| n-Tricosane | 3.63 | 89.7 | 89.7–99.2 | 125–130 | " |
| n-Decosane | 5.14 | 84.2 | 84.2–98.7 | 122–125 | " |
| n-Heneicosane | 2.12 | 79.8 | 79.8–98.2 | 120–125 | " |
| n-eicosane | 0.78 | 64.3 | 64.3–97.2 | 120–125 | " |
| Components not forming complex with carbamide | 85.77 | — | — | — | — |

After isolating all the above-cited n-alkanes the pour point temperature of the petroleum fraction residue lowers down to 2.0° C.

Temperatures of the upper complexation limit for individual n-alkanes are given in Table 3 and the temperature gradients $a_i$ for the equation in Table 4.

Table 3

| Number of carbon atoms in the molecule of n-alkane | Temperature of the upper limit of complexation of individual n-alkane with carbamide, ° C. |
|---|---|
| 6 | 28.0 |
| 7 | 38.0 |
| 8 | 48.0 |
| 9 | 58.0 |
| 10 | 68.0 |
| 11 | 73.9 |
| 12 | 78.5 |
| 13 | 82.6 |
| 14 | 86.0 |
| 15 | 88.7 |
| 16 | 91.0 |
| 17 | 93.1 |
| 18 | 94.7 |
| 19 | 95.9 |
| 20 | 97.2 |
| 21 | 98.2 |
| 22 | 98.7 |
| 23 | 99.2 |
| 24 | 99.7 |

Table 4
Cumulative Table of Constant Gradients of Main equations for Calculating the Upper Limit of complexation

| Components | n-Decane | n-Undecane | n-Dodecane | n-Tridecane | n-Tetradecane | n-Pentadecane | n-Hexadecane | n-Heptadecane | n-Octadecane | n-Nonadecane | n-Eicosane | n-Heneicosane | n-Docosane | n-Tricosane | n-Tetracosane |
|---|---|---|---|---|---|---|---|---|---|---|---|---|---|---|---|
| n-Tricosane | | | | | | | | | | | | | | — | 0.00035 |
| n-Docosane | | | | | | | | | | | | | — | 0.00070 | 0.00260 |
| n-Heneicosane | | | | | | | | | | | | — | 0.00100 | 0.00300 | 0.00485 |
| n-Eicosane | | | | | | | | | | | — | 0.00135 | 0.00345 | 0.00535 | 0.00710 |
| n-Nonadecane | | | | | | | | | | — | 0.00170 | 0.00395 | 0.00590 | 0.00770 | 0.00935 |
| n-Octadecane | | | | | | | | | — | 0.00200 | 0.00440 | 0.00645 | 0.00835 | 0.01005 | 0.01160 |
| n-Heptadecane | | | | | | | | — | 0.00235 | 0.00460 | 0.00710 | 0.00905 | 0.01080 | 0.01240 | 0.01385 |
| n-Hexadecane | | | | | | | — | 0.00270 | 0.00535 | 0.00770 | 0.00980 | 0.01165 | 0.01325 | 0.01475 | 0.01610 |
| n-Pentadecane | | | | | | — | 0.00300 | 0.00590 | 0.00835 | 0.01050 | 0.01250 | 0.01415 | 0.01470 | 0.01710 | 0.01835 |
| n-Tetradecane | | | | | — | 0.00335 | 0.00640 | 0.00910 | 0.01135 | 0.01340 | 0.01520 | 0.01675 | 0.01815 | 0.01945 | 0.02060 |
| n-Tridecane | | | | — | 0.00370 | 0.00695 | 0.00980 | 0.01230 | 0.01435 | 0.01620 | 0.01790 | 0.01935 | 0.2060 | 0.2180 | 0.02285 |
| n-Dodecane | | | — | 0.00400 | 0.00760 | 0.01065 | 0.01320 | 0.01550 | 0.01735 | 0.01910 | 0.02060 | 0.02185 | 0.02305 | 0.02415 | 0.02510 |
| n-Undecane | | — | 0.00435 | 0.00830 | 0.01160 | 0.01435 | 0.01670 | 0.01870 | 0.02035 | 0.02190 | 0.02330 | 0.02445 | 0.02550 | 0.02650 | 0.02735 |
| n-Decane | — | 0.00470 | 0.00905 | 0.01270 | 0.01560 | 0.01805 | 0.02010 | 0.02190 | 0.02335 | 0.02470 | 0.02600 | 0.02705 | 0.02795 | 0.02885 | 0.02960 |
| n-Nonane | 0.00500 | 0.01000 | 0.01385 | 0.01700 | 0.01960 | 0.02165 | 0.02350 | 0.02510 | 0.02635 | 0.02760 | 0.02870 | 0.02965 | 0.03040 | 0.3120 | 0.03185 |
| n-Octane | 0.01100 | 0.01530 | 0.01855 | 0.02130 | 0.02360 | 0.02535 | 0.02700 | 0.02830 | 0.02935 | 0.03050 | 0.03141 | 0.03215 | 0.03285 | 0.03355 | 0.03410 |
| n-Heptane | 0.01700 | 0.02060 | 0.02335 | 0.02560 | 0.02760 | 0.02905 | 0.03040 | 0.03150 | 0.03235 | 0.03330 | 0.03410 | 0.03475 | 0.03530 | 0.03590 | 0.03635 |
| n-Hexane | 0.02300 | 0.02590 | 0.02815 | 0.3000 | 0.03160 | 0.03275 | 0.03380 | 0.03470 | 0.03535 | 0.03620 | 0.03680 | 0.03735 | 0.03775 | 0.03825 | 0.03860 |
| Hydrocarbons not forming complex | 0.03000 | 0.03200 | 0.03365 | 0.03500 | 0.03610 | 0.03695 | 0.03770 | 0.03840 | 0.03895 | 0.03950 | 0.03990 | 0.04035 | 0.04070 | 0.04100 | 0.04125 |

What is claimed is:

1. A method of isolating individual normal alkanes from petroleum stock, which comprises contacting said petroleum stock with crystalline carbamide in the presence of an activator at a temperature which is the upper limit for complex formation of the individual normal alkane to be isolated, said alkane having the maximum molecular weight of the alkanes in said petroleum stock, thereby forming a complex of said alkane with the carbamide; removing the residual stock from the formed complex; washing the complex with an individual normal alkane which is the same as the alkane being isolated; heating said complex to a temperature 2°–5° C higher than its decomposition point; recovering the individual normal alkane having the maximum molecular weight in said petroleum stock from said complex; and recycling the residual petroleum stock and recovering the remaining individual normal alkanes in succession in order of decreasing molecular weight by the above steps.

* * * * *